United States Patent [19]

Laurent

[11] Patent Number: 5,401,776
[45] Date of Patent: Mar. 28, 1995

[54] USE OF MODAFINIL FOR THE TREATMENT OF URINARY AND FECAL INCONTINENCE

[75] Inventor: Philippe Laurent, Oullins, France

[73] Assignee: Laboratoire L. Lafon, Maisons Alfort, France

[21] Appl. No.: 137,417

[22] Filed: Oct. 18, 1993

[30] Foreign Application Priority Data

Oct. 23, 1992 [FR] France ............... 92 12700

[51] Int. Cl.⁶ .......................................... A61K 31/165
[52] U.S. Cl. ................................................ 514/618
[58] Field of Search ...................................... 514/618

[56] References Cited

U.S. PATENT DOCUMENTS

| | | | |
|---|---|---|---|
| 4,177,290 | 12/1979 | Lafon | 546/234 |
| 4,927,855 | 5/1990 | Lafon | 514/618 |
| 5,180,745 | 1/1993 | Lafon | 514/618 |

FOREIGN PATENT DOCUMENTS 0462004 12/1991 European Pat. Off.
2385693 2/1978 France.

*Primary Examiner*—Raymond Henley, III
*Assistant Examiner*—K. Waddington

[57] ABSTRACT

The present invention relates to the use of modafinil for the manufacture of a medicinal product for the treatment of urinary and fecal incontinence and urethrovesical and anal sphincteral disorders.

1 Claim, No Drawings

USE OF MODAFINIL FOR THE TREATMENT OF URINARY AND FECAL INCONTINENCE

The present invention relates to a new therapeutic use of modafinil.

Modafinil or (benzhdrylsulfinyl)aoetamide is a compound of formula

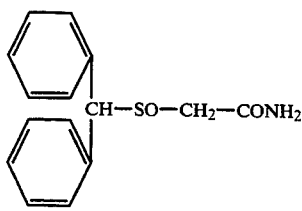

This compound and its therapeutic use as active agent on the central nervous system as non-amphetamine psycho-stimulant have been described in Patent FR-A-2,385,693.

The levorotatory and dextrorotatary isomers of modafinil have also been described in Patent EP-A-0,233,106.

It has now been discovered that modafinil and its isomers possess a pharmacological effect on the musculosphincteral system of the vesicourethral urinary apparatus and on the motricity of the external anal sphincter as well as a therapeutic effect in vesicourethral urinary and/or fecal continence disorders.

Consequently, the subject of the present invention is the use of modafinil for the manufacture of a medicinal product for the treatment of urinary and fecal incontinence and urethrovesical and anal sphincteral disorders.

The modafinil-containing medicinal product may be provided especially in a form suitable for oral administration. Generally, the administered doses may be from 1 mg/kg to 100 mg/kg and preferably from 5 to 100 mg/kg.

The results of pharmacological, pharmacoclinical and clinical trials demonstrating the effects of modafinil on the sphinteral activity as well as on urinary and/or fecal incontinence of neurological origin will be given below.

1) Study of sphincteral reactivity by means of urodynamic measurements on adult and elderly patients with vesicosphincteral disorders associated with a cervicosphincteral insufficiency, exclusive or otherwise.

The objective of this study was to study the effect of modafinil administered in a single dose, according to a blind design relative to a placebo, on the sphincteral reactivity measured by the urethral pressure profile in patients suffering from vesicosphincteral disorders.

The method used, designated "urethral pressure profile", also called sphincterometry, consists in the study of the urethral pressures recorded by means of a catheter gradually withdrawn from the bladder as far as the urethral meatus. This method is described in detail in A. R. Murphy, T. P. Stephenson, A. J. Wein "Urodynamics: principles, practice and application" Churchil Livingstone Ed. Edinburg 1984, 1 vol. 394 p; and Monographie SIFUD "Urodynamique et neuro-urologie" FIIS Ed. Paris, 1988, 1 vol. 256 p.

The urethral profile method measures the maximum urethral pressure (M.U.P.), the maximum closing pressure which is the difference between the maximum urethral pressure and the pressure existing inside the bladder at a given vesical filling level, and finally the total length of the profile or functional length. The water Electromed apparatus was used.

The measurements were performed on an empty bladder on the one hand and a full bladder on the other hand.

The patients, of female sex, received respectively, as a single dose, either 400 mg of modafinil, or a placebo.

Table I gives the results relating to the maximum urethral pressure (M.U.P.) in cm of water.

TABLE I

|         | MODAFINIL 400 mg (n = 24) | PLACEBO (n = 24) |
| --- | --- | --- |
| T0 (9 h)  | 36.6 ± 8.4  | 39.7 ± 9.6  |
| T1 (10 h) | 37.8 ± 10.1 | 39.9 ± 10.5 |
| T2 (11 h) | 40.1 ± 11.3 | 39.7 ± 10.8 |
| T3 (12 h) | 40.1 ± 10.5 | 38.3 ± 10.7 |

Table II gives the results relating to the maximum closing pressure (in cm of water).

TABLE II

|         | MODAFINIL 400 mg (n = 24) | PLACEBO (n = 24) |
| --- | --- | --- |
| T0 (9 h)  | 29.3 ± 9.0  | 32.3 ± 9.5  |
| T1 (10 h) | 30.0 ± 10.7 | 32.9 ± 9.9  |
| T2 (11 h) | 32.2 ± 12.3 | 32.9 ± 10.3 |
| T3 (12 h) | 32.9 ± 11.4 | 31.4 ± 10.2 |

The results indicate a significant increase in the maximum closing pressure and the maximum urethral pressure with modafinil compared with the placebo which did not, for its part, result in a variation.

2) Double blind evaluation of the effect of modafinil in urinary incontinence of neurological origin This study was performed on 40 subjects (average age 10.77 years) with a urinary incontinence of neurological origin, who had already been treated or otherwise with modest success (anticholinergics).

Modafinil was prescribed at the dosage of 10 mg/kg (mornings and evenings), according to a double blind design relative to the placebo.

Before inclusion, the patients were divided into two subgroups (reactive and non-reactive) according to their response to pharmacological tests (determination of the modification of vesical closing pressure after single administration of 10 mg/kg of modafinil.

The allocation of the treatments was balanced in each of these subgroups (10 treated and 10 controls).

The trial lasted for 6 weeks, the first two without treatment. The principal instrument for evaluation was a micturition calendar completed daily which made it possible to quantify the night continence, the number of dry periods per day, the number of leaks per day and per hourly periods of two hours.

After checking that the Treated and Control groups were comparable during the two reference weeks, we were able to show that modafinil, at the dosage of 10 mg/kg, is capable of improving, over the short term, contrary to the placebo, night continence (this difference disappears after two weeks) and, over the long term (4 weeks), diurnal, especially morning, urinary leaks.

It should be noted that the therapeutic effect was greater in patients who were reactive to the pharmacological test for inclusion. This "responding" effect was demonstrated independently of the "treatment" effect.

The statistical independence between the "responding" effect and the "treatment" effect makes it possible to conclude that modafinil has real efficacy.

3) Study of the effects of modafinil on the motricity of the external anal sphincter Materials and method 1—anesthesia This study was performed on 6 cats of both sexes, with an average weight of 2.5 kg, anesthetized with chloralose at the dose of 75 to 80 mg/kg. The cardiac rhythm and the blood pressure are recorded during the whole experiment in order to detect a possible modification in the level of anesthesia.

2—Access to the external anal sphincter

It is made via the posterior route by making an incision in the skin above and on both sides of the anal orifice. The lateral and dorsal parts of the sphincter are separated from the adipose tissue surrounding them.

3—Dissection of the pudendal nerves

They are situated laterally relative to the sphincter. A pudendal nerve is dissected over about one centimeter and then severed, its central end is then placed on stimulating electrodes enclosed in a plexiglass trough.

4—Stimulation technique

The stimulations were performed on the central end of a severed pudendal nerve so as to obtain reflex responses which alone, are facilitated by noradrenalin. In another experiment, the peripheral end of this severed nerve was stimulated so as to stimulate the sphincteral efferences and to obtain a direct response. The impulses, provided by a stimulator (Grass S88), are rectangular shocks which last for 0.1 ms; their intensity varies according to the animal, but it is determined such that the amplitude of the responses is inframaximal.

5—Technique for receiving the electromyographic activity

In order to record the sphincteral responses to the stimulation of the pudendal nerve, bipolar derivations of the electrical activity of the external anal sphincter are made by means of electrodes implanted in the muscle according to the technique of Basmadjian and Stecko (J. Appl. Physiol. 17, 749, 1962). The interelectrode distance is as long as possible so as to pick up responses which represent the activity of a large number of motor units. The electrical activity, recorded by means of an amplifier (ECEM, amplifier with RC link, pass-band 0.120 Hz, time constant 2s), is transmitted to an analog to digital converter. The signals thus converted are processed by a computer (Macintosh) by means of appropriate software (MacLab). The recorded response of the external anal sphincter corresponds to the mean of 5 successive responses.

6—Routes of administration

Modafinil was injected intravenously at the dose of 5 mg/kg, after dilution in an appropriate solvent.

RESULTS

It was checked that the intravenous injection of the solvent, at a dose identical to that used to dissolve the modafinil, did not induce any effect on the responses of the external anal sphincter to the stimulation of a pudendal nerve.

Modafinil, at the dose of 5 mg/kg i.v., brings about an increase in the amplitude of the reflex response of the external anal sphincter. The results are given in Table III.

TABLE III

Characteristics of the effects of modafinil on the reflex response of the external anal sphincter

| Latency (min) | Duration (min) | Increase in the amplitude of the response (n = 3) |
|---|---|---|
| 10.00 + 5.00 (n = 3) | 18.70 ± 6.00 (n = 3) | 76.70 ± 20.00 (n = 3) |

The intravenous injection of modafinil thus brings about a facilitation of the sacral spinal reflex responsible for the tonic activity of the external anal sphincter.

I claim:

1. A method for the treatment of urinary and/or fecal incontinence which comprises administering to a patient in need thereof a therapeutically effective amount of a compound selected from modafinil and its optical isomers.

* * * * *